(12) United States Patent
Keita et al.

(10) Patent No.: US 9,200,931 B2
(45) Date of Patent: Dec. 1, 2015

(54) MEASURING TRANSDUCER OF VIBRATION-TYPE FOR A FLUID FLOWING IN A FLEXIBLE HOSE

(75) Inventors: Mamadi Keita, Basel (CH); Mike Touzin, Hollstein (DE); Antoine Simon, St. Louis (FR)

(73) Assignee: Endress + Hauser Flowtec AG, Reinach (DE)

( * ) Notice: Subject to any disclaimer, the term of this patent is extended or adjusted under 35 U.S.C. 154(b) by 265 days.

(21) Appl. No.: 13/884,403

(22) PCT Filed: Oct. 20, 2011

(86) PCT No.: PCT/EP2011/068362
§ 371 (c)(1),
(2), (4) Date: Jul. 19, 2013

(87) PCT Pub. No.: WO2012/062550
PCT Pub. Date: May 18, 2012

(65) Prior Publication Data
US 2014/0000383 A1    Jan. 2, 2014

(30) Foreign Application Priority Data

Nov. 10, 2010  (DE) .......................... 10 2010 043 707

(51) Int. Cl.
*G01F 1/84* (2006.01)
*G01F 1/32* (2006.01)
(Continued)

(52) U.S. Cl.
CPC ............ *G01F 1/3227* (2013.01); *G01F 1/8404* (2013.01); *G01F 1/845* (2013.01); *G01F 1/8409* (2013.01); *G01F 1/8472* (2013.01);
(Continued)

(58) Field of Classification Search
None
See application file for complete search history.

(56) References Cited

U.S. PATENT DOCUMENTS 5,179,862 A    1/1993  Lynnworth
5,663,509 A *  9/1997  Lew et al. ................ 73/861.357
(Continued)

FOREIGN PATENT DOCUMENTS

DE         4311694 C1      9/1994
DE        19819753 A1     11/1999
DE    102008002215 A1     12/2009
(Continued)

OTHER PUBLICATIONS

German Search Report, German Patent Office, Munich, Jun. 8, 2011.
(Continued)

*Primary Examiner* — Harshad R Patel
(74) *Attorney, Agent, or Firm* — Bacon & Thomas, PLLC

(57) ABSTRACT

The present invention relates to a measuring transducer of the vibration-type for a fluid flowing in a flexible hose. The measuring transducer includes, a hose carrier unit, which has at least sectionally a loop-shaped outer contour, around which a flexible hose can be led. Furthermore, the measuring transducer includes a clamping unit, by which a flexible hose led in use around the loop-shaped outer contour is tightenable against the loop-shaped outer contour, at least one exciter coupled to the hose carrier unit, by which the hose carrier unit is excitable to execute mechanical oscillations, which are accompanied by alternating elastic deformation of the hose carrier unit, and at least one oscillation sensor, by which mechanical oscillations of the hose carrier unit and/or a flexible hose installed in use in the measuring transducer are registerable.

17 Claims, 1 Drawing Sheet

(51) Int. Cl.
*G01N 9/00* (2006.01)
*G01N 11/16* (2006.01)

(52) U.S. Cl.
CPC .............. *G01F1/8477* (2013.01); *G01N 9/002* (2013.01); *G01N 11/16* (2013.01)

(56) References Cited

U.S. PATENT DOCUMENTS

2009/0078047 A1 3/2009 Dam

2011/0079091 A1 4/2011 Keita

FOREIGN PATENT DOCUMENTS

JP 7-15397 2/1995
WO 2008056976 A1 5/2008

OTHER PUBLICATIONS

International Search Report, EPO, The Netherlands, Dec. 21, 2011.
English translation of IPR, WIPO, Geneva, May 23, 2013.

* cited by examiner

ID> MEASURING TRANSDUCER OF VIBRATION-TYPE FOR A FLUID FLOWING IN A FLEXIBLE HOSE

TECHNICAL FIELD

The present invention relates to a measuring transducer of the vibration-type for a fluid flowing in a flexible hose. The term "flexible hose" is intended herein to include flexible tubes and flexible tubing. The measuring transducer is, in such case, embodied especially for application in a Coriolis, flow measuring device. As is generally known from the technical field, in Coriolis, flow measuring devices, the Coriolis principle is utilized, according to which an additional force, the Coriolis force, acts on a mass when the mass executes in a system superimposed movements of a rotation and a straight line movement extending at least partially perpendicular to the rotational axis.

BACKGROUND DISCUSSION

Flow measuring devices are, as a rule, embodied as in-line measuring devices, which are insertable into a pipeline, such as, for example, into a process line of an industrial plant. Such flow measuring devices have, as a rule, at least one measuring tube, through which fluid flows during use. A Coriolis, flow measuring device can measure at least one parameter, such as, for example, mass flow rate, density, viscosity, etc., of the fluid flowing in the pipeline.

In some applications, there is the problem that the fluid to be measured tends to form accretions, is abrasive and/or attacks the material of the at least one measuring tube of a flow measuring device. This leads to the fact that the measuring tube must be relatively frequently replaced. In typical Coriolis, flow measuring devices, this is associated with significant effort and high costs. In some fields of application, such as, for example, in the foods industry, there is, furthermore, the requirement that the total system of pipelines contacted by the fluid, thus also the at least one measuring tube of an installed flow measuring device, must, after a certain duration of operation and/or in the case of a change of the fluid flowing through the system, be cleaned. This is in the case of measuring tubes of flow measuring devices, especially in the case of measuring tubes of Coriolis, flow measuring devices, complex and cost intensive. Furthermore, there is, in some fields of application, such as, for example, in medicinal fields, the requirement that the respective fluid lines, whose flow should be determined, should not have their continuity interrupted. An example of such a fluid carrying line is an infusion hose, which is, as a rule, formed of a flexible plastic tube.

Known from German publication DE 10 2008 002 215 A1 is a Coriolis, flow measuring device, in the case of which a guide unit, through which the fluid to be measured flows, is placed removably on a support unit. The guide unit and the support unit are mechanically coupled to one another. The support unit is excited in use to mechanical oscillations and the mechanical oscillations of the support unit are registered by at least one oscillation sensor. The construction described in DE 10 2008 002 215 A1 is suited especially for flow measurement of gravitationally transported solids (e.g. bulk goods).

Known from German publication DE 43 11 694 C1 is a mass flow meter working according to the Coriolis principle, which has a soft, essentially completely flexible, hose, which is secureable by force interlocking, e.g. friction interlocking, with a predetermined track on a rigid hose accommodation. The hose accommodation is, in turn, secured to an oscillatory system for movement together with the hose about a first axis. Furthermore, the hose accommodation is held rotatably relative to the oscillatory system about a second axis in such a manner that the hose accommodation can execute movement around the second axis brought about by the Coriolis forces of the mass flowing in the hose. Due to the different rotational axes, this arrangement leads to a relatively complex construction.

SUMMARY OF THE INVENTION

Accordingly, an object of the present invention is to provide a measuring transducer for a flow measuring device, in the case of which a complex cleaning of the at least one measuring tube is avoided and by which, when required, also a fluid flowing in a fluid carrying line is measurable, without requiring interruption of the continuity of the fluid carrying line.

The object is achieved by a measuring transducer of the vibration-type provided for a fluid flowing in a flexible hose. The measuring transducer includes a hose carrier unit, which has at least sectionally a loop-shaped outer contour, around which a flexible hose can be led, a clamping unit, by which a flexible hose led in use around the loop-shaped outer contour, is tightenable against the loop-shaped outer contour, at least one exciter coupled to the hose carrier unit, by which the hose carrier unit is excitable to execute mechanical oscillations, which are accompanied by alternating elastic deformation of the hose carrier unit, and at least one oscillation sensor, by which mechanical oscillations of the hose carrier unit and/or a flexible hose installed in use in the measuring transducer are registerable.

In the present invention, a measuring transducer of vibration-type is provided for a fluid flowing in a flexible hose. The measuring transducer includes a hose carrier unit, which has at least sectionally a loop-shaped outer contour, around which a flexible hose can be led, a clamping unit, by which a flexible hose led in use around the loop-shaped outer contour, is tightenable against the loop-shaped outer contour, at least one exciter coupled to the hose carrier unit, by which the hose carrier unit is excitable to execute mechanical oscillations, which are accompanied by alternating elastic deformation of the hose carrier unit, and at least one oscillation sensor, by which mechanical oscillations of the hose carrier unit and/or a flexible hose installed in use in the measuring transducer are registerable.

Through the construction of the measuring transducer of the invention, a flexible hose can be simply and rapidly inserted into, and removed from, the measuring transducer. The measuring transducer of the invention provides, in such case, the opportunity for flow measurement (e.g. mass flow, density of the fluid, etc.) with a single-use sensor system, which means that the component(here: the flexible hose) coming in contact with fluid can be simply discarded after use and replaced by a new one. In this way, the flexible hose to be installed in the measuring transducer is providable as a cost effective, consumed part (i.e. a disposable article). Instead of a complex cleaning, when required, the flexible hose can be simply replaced. Furthermore, the construction of the invention enables that the flexible hose is in the case of aggresive or abrasive media frequently replaceable and without great cost. Moreover, the measuring transducer can, in simple manner, be so formed that an existing flexible hose, such as, for example, an infusion hose applied for medicinal purposes, can be rapidly and simply inserted into the measuring transducer, without requiring that the continuity of the flexible hose must be interrupted for this. Construction and operation of the measuring transducer of the invention are simple. Especially, the use of components pivoting or moving relative to one another is omitted, which makes the measuring transducer cost effective for manufacture and robust in use. The oscillations required for Coriolis, mass flow measurement or for a Coriolis, density measurement are exclusively produced by an alternating, elastic deformation of the hose carrier unit.

The measuring transducer of the invention of the vibration-type is especially embodied for use in a Coriolis, flow measuring device. Such a Coriolis, flow measuring device can register especially mass flow and/or density of a flowing fluid. A functional principle of Coriolis, flow measurement in a Coriolis, flow measuring device with a measuring transducer of the invention is, in such case, that the flexible hose, through which the fluid is flowing, is excited to execute mechanical oscillations via the oscillations of the hose carrier unit. Due to the superimposing of the oscillations with the flow movement of the fluid, there acts on the fluid flowing in the flexible hose a Coriolis force. This Coriolis force is directed at at least a first region along the length of the oscillating flexible hose oppositely to that at a second region along the length. If the oscillations of the flexible hose and/or the hose carrier unit are registered by at least one oscillation sensor at at least two oscillation measurement points spaced from one another along the length of the flexible hose, then, due to the Coriolis force acting on the flowing fluid, a phase shift of the oscillations can be registered. This phase shift is proportional to the mass flow through the flexible hose. Additionally or alternatively to mass flow, such a Coriolis, flow measuring device can also determine a density of the flowing fluid. In such case, the principle is utilized that the resonant frequency of the excited oscillation depends on the oscillating mass and therewith on the density of the fluid flowing in the flexible hose. By readjusting the excitation frequency in such a manner that the oscillatory system is excited in its resonant frequency, the resonant frequency and therefrom, in turn, the density of the flowing fluid can be determined. Additionally or alternatively, such a Coriolis, flow measuring device can perform other functions, especially bubble detection or detection of other localized contaminations. The exciting by the at least one exciter is, in such case, especially controlled by an electronics of the Coriolis, flow measuring device. Furthermore, the electronics evaluates the sensor signals provided by the at least one oscillation sensor.

The "fluid" can be a gas or a liquid, which, depending on the application, can also have different viscosities. The gas can, in such case, also contain solid particles, such as, for example, pneumatically transported dust, or liquid fractions. Furthermore, a liquid can also entrain gas inclusions (bubbles) or solid particles. Gravitationally transported solids are not referred to as "fluids". In a further development of the invention, the fluid is a liquid.

The terminology "flexible hose" means a hose, which is movable in the direction transverse to its direction of elongation. This means especially, as explained below in reference to a further development, that the hose has along its direction of elongation a relatively low bending stiffness. The flexible hose need not, in such case, be absolutely elastic. In reference to the application of the flexible hose around the hose carrier unit in tightened state, however, elastic properties are advantageous, especially along the direction of elongation of the flexible hose.

The terminology, loop-shaped outer contour, means a curve, which has essentially a U-shape. In such case, the U-shape in the region of the upper ends of the "U", which are formed, respectively, by a hose entrance and a hose exit, can, compared with a central region of the U-shape, be narrowed or, alternatively, even widened. As explained below in reference to a form of embodiment of the invention, a narrowing in the region of the upper ends of the "U" is advantageous as regards symmetry characteristics. Especially, the loop shape is embodied in such a manner that the separation between the two loop arms goes from a minimum separation (in the region of the hose entrance and hose exit) to a maximal separation (in a central region of the hose carrier unit) and then narrows again toward the reversal point of the loop-shaped outer contour. The terminology "at least sectionally loop-shaped outer contour" does not exclude that the hose carrier unit has at sections, where a hose led around the loop-shaped outer contour does not lie on the hose carrier unit, a differently formed outer contour. For example, the hose carrier unit can, as a whole, have an oval or elliptically formed, outer contour.

In connection with the present invention, the terminology "flexible hose installed in the measuring transducer" means a flexible hose, which in the (in claim 1) claimed arrangement is led around the loop-shaped outer contour and clamped. The tension of the hose clamped against the loop-shaped outer contour is preferably selected in such a manner that the flexible hose and the hose carrier unit are connected to one another relative to oscillations. This means, especially, that the hose carrier unit, excited to execute oscillations, excites the flexible hose to corresponding oscillations. Furthermore, especially when the oscillation measurement points are provided on the hose carrier unit, the tension is sufficiently high that the phase shift of the flexible hose brought about by the Coriolis force is transmittable to the hose carrier unit. In addition to tension, also other coupling can be provided between the hose carrier unit and the flexible hose. This other coupling can be, for example, an adhesive connection, an engagement of the flexible hose in a corresponding gutter provided in the hose carrier unit, etc. If another coupling is provided, then the tension can be selected correspondingly lower (for example, only so high that the hose lies against the loop-shaped outer contour). In a further development, the coupling between the hose carrier unit and the flexible hose occurs exclusively from the tension of the flexible hose produced by the clamping unit.

The exciting of the hose carrier unit to execute mechanical oscillations by the at least one exciter can occur in various ways, especially electromechanically, capacitively, etc. In corresponding manner, the registering of the mechanical oscillations can also occur in different ways, especially electromechanically, capacitively, optically, etc. In such case, the mechanical oscillations of the hose carrier unit can be registered or also, directly, the mechanical oscillations of the flexible hose.

The present invention relates also to a measuring transducer, in which a flexible hose is inserted in the arrangement.

In a further development, the hose carrier unit and the hose course of a flexible hose installed in use in the measuring transducer extend mirror symmetrically with reference to a symmetry plane. The symmetry plane extends, in such case, between a hose entrance of the hose carrier unit and a hose exit from the hose carrier unit, extends from a reversal point of the loop-shaped outer contour located opposite the hose entrance and hose exit and is, furthermore, perpendicular to a loop plane, which is defined by the loop shape of a flexible hose installed in use in the measuring transducer. As will be explained below in detail, such symmetry enables yet other functionalities, such as, for example, bubble detection.

In a further development, the hose carrier unit has, in a loop plane defined by the loop shape of a flexible hose installed in use in the measuring transducer, a closed shape, especially an oval shape. Especially, a cross sectional area of the hose carrier unit has a closed shape in the plane of the loop. In this way, a stable, robust and compact embodiment of the hose carrier unit is implemented. Instead of an oval shape, basically also a circularly round shape provides an option. Advantageously, an oval, especially elliptical shape, is used, wherein, in this case, it is preferred that the ratio of UR, wherein L is the longer half axis of the ellipse and R is the larger radius of curvature of the ellipse, is greater than zero and much smaller than 1 ($0<L/R<<1$). Furthermore, it is preferred that a bending stiffness of the hose carrier unit along its loop-shaped outer contour (apart from regions, where a still to be described securement is provided) is essentially constant.

In a further development, it is provided that the at least one exciter and/or the at least one oscillation sensor is/are arranged inwardly of the hose carrier unit. In this way, a compact formation of the measuring transducer is implemented. Furthermore, the exciter and/or the oscillation sensor are protected in this way. The terminology "inwardly" refers to the oppositely lying side of the flexible hose installed in use in the measuring transducer. If the hose carrier unit has a closed shape, then the enclosed components are preferably arranged in a free space formed within the closed shape. Preferably, all exciters and oscillation sensors are arranged inwardly of the hose carrier unit.

In a further development, the hose carrier unit is divided into two oscillatory systems arranged mirror symmetrically to one another relative to the symmetry plane. This is accomplished by a securement arranged on the symmetry plane in the region of the hose entrance and the hose exit as well as by a securement arranged on the symmetry plane in the region of the reversal point Due to this provision of two serially flowed-through, oscillatory systems, a redundancy is provided with reference to the performing of flow measurements, which enables additional functionalities, especially a detection of localized impurities entrained in the fluid. A securement suppresses, in such case, oscillations in the respective region of the hose carrier unit. The securement can be provided, for example, to a housing or a carrier component of the measuring transducer, especially inwardly of the hose carrier unit. Supplementally to the securements, there can also be provided outside of the hose carrier unit at least one hose securement for a flexible hose installed in use in the measuring transducer. Such hose securements arranged, preferably, in each case, opposite a securement of the hose carrier unit suppress oscillations of the hose in the region of the hose securement. The hose securement provides that a flexible hose applied especially in the measuring transducer is pressed against the hose carrier unit. At the same time, the hose should not be completely or excessively collapsed by the hose securement, so that no too large flow resistance arises thereby.

In a further development, the two oscillatory systems are excitable to mutually (mirror) symmetric oscillations by the at least one exciter by alternating enlarging and reducing of the separation of the arc sections of the hose carrier unit extending between the securements. Accordingly, the measuring transducer has in use two identical, mutually (mirror) symmetrically oscillating, oscillatory systems, with which, in each case, a Coriolis, mass flow measurement, a density measurement, etc. is/are performable. These two oscillatory systems are flowed through in series by the flowing fluid, so that a redundancy is present as regards these measurements. The excitation can, among others, occur by way of an exciter extending between the two arc sections, wherein the length of the exciter is periodically changeable. Furthermore, for example, also two exciters can be provided, which are supported on one side, in each case, relative to a carrier component arranged between the two arc sections and on the other side, in each case, on an associated arc section. The lengths of both exciters are periodically changeable.

In a further development, there are associated with each oscillatory system, in each case, two oscillation sensors, which, in each case, are arranged spaced from one another along the associated arc section of the hose carrier unit extending between the securements. In this way, for each oscillatory system, a phase shift between an inlet side and an output side section of such oscillatory system can be registered. Accordingly, a Coriolis, mass flow measurement can be performed in each oscillatory system.

In a further development, the two oscillatory systems, with reference to the arrangement of the oscillation measurement points of the at least one oscillation sensor and with reference to the excitation points of the at least one exciter, are embodied mirror symmetrically to one another relative to a symmetry plane. The terminology "oscillation-measuring point" means, in such case, the point of the hose carrier unit and/or of the flexible hose, at which an oscillation of such, or of the same, is registered. The terminology "excitation point" means, in corresponding manner, the point on the hose carrier unit, where the exciting of such to execute oscillations occurs. This symmetry relationship is, in such case, independent of the concrete arrangement and formation of the associated exciter and oscillation sensor(s). Preferably, however, also the exciter as well as the oscillation sensors fulfill the above stated symmetry relationship.

In a further development, the hose carrier unit, the predetermined course of a flexible hose installed in use in the measuring transducer, apart from the region of the hose entrance and the hose exit and the region of the reversal point, the arrangement of the oscillation measurement points of the at least one oscillation sensor, and/or the arrangement of the excitation points of the hose carrier unit by the at least one exciter, are mirror symmetric relative to a plane extending perpendicular to the symmetry plane and perpendicular to the loop plane. Due to this symmetry, essentially identical Coriolis, mass flow measurements, density measurements, etc. can be performed in the two oscillatory systems. Since fluid flows through the two oscillatory systems in series, a fundamental redundancy is present. Arising deviations between the two oscillatory systems can be evaluated supplementally, such as, for example, for bubble detection or, in general, for detection of localized impurities. The excitation points can lie, in such case, especially on the above said plane (extending perpendicular to the symmetry plane and perpendicular to the loop plane). Furthermore, it is especially provided that each oscillatory system has, in each case, on both sides of the plane, one (or, in given cases, even a number of) oscillation measuring point(s). In case the hose carrier unit is oval or elliptical, then preferably the longer half axis of the ellipse extends perpendicularly to the plane (and within the symmetry plane) and the shorter half axis extends within the plane. As is mentioned above, there arises, in the case of the course of a flexible hose installed in use in the measuring transducer, a deviation from the symmetry, respectively, in the region of the hose entrance and the hose exit on the one side and in the region of the reversal point on the other side. In reference to the oscillations, these symmetry deviations can be largely suppressed by largely suppressing oscillations in these regions (by corresponding securements and, in given cases, additional hose securement).

In a further development, the hose carrier unit includes a gutter extending along the loop shaped, outer contour for accommodating a flexible hose installed in use in the measuring transducer. In this way, a better hold of the flexible hose on the hose carrier unit is assured. The gutter is, in such case, preferably matched to the pertinent hose shape. The hose can have, among others, a round or oval, cross section. In the case of an oval cross section, the hose lies preferably in the region with the greater radius of curvature on the hose carrier unit, especially in the gutter. The shape of the gutter is preferably matched to the shape of the hose. The gutter can, in such case, also be embodied in such a manner that it at least in some sections narrows at the top, so that the hose has to be pressed with force into the gutter and engages with the gutter, so that it is subsequently held therein.

In a further development, the flexible hose is formed at least partially of a flexible, synthetic (e.g. plastic) material and/or a flexible weave. In such case, also natural, flexible materials, such as, for example, natural rubber, provide options. The flexible hose can, in such case, be formed completely of a flexible, synthetic material and/or a flexible weave. It can, however, also be reinforced by a further material, such as, for example, a metal helix. Reinforcement can prevent or lessen a squeezing together, or collapsing, of the flexible hose in the course of its use. In this connection, it is to be noted that a squeezing together of the hose basically has no disadvantageous effect on the Coriolis, mass flow measurement. It can, however, among others as regards flow resistance, be preferred that the hose not, or only a little, be squeezed together.

In a further development, the hose carrier unit has a clearly higher bending stiffness than the flexible (empty) hose. The greater this ratio is, the greater is the accuracy of measurement (for example, a Coriolis, mass flow measurement or a density measurement). Preferably, bending stiffness of the (empty) hose along its direction of elongation (in reference to forces acting transversely to the direction of elongation) is negligible in comparison to bending stiffness of the hose carrier unit along its loop-shaped outer contour (in reference to forces acting transversely to the loop-shaped outer contour). In a further development, a ratio of the bending stiffness of the hose carrier unit along the loop-shaped outer contour to the bending stiffness of the flexible (empty) hose along its direction of elongation is at least 10. Preferably, the ratio is at least 100. The bending stiffness, whose units are $Nm^2$, is, in such case, as known in the technical field, formed by the product of the modulus of elasticity and the areal moment of inertia (here relative to a cross sectional area perpendicular to the direction of elongation of the hose, or perpendicular to the loop-shaped outer contour of the hose carrier unit). These ratio values hold, in such case, preferably over the total course of the loop-shaped outer contour. In a further development, the hose carrier unit is formed of a metal material, such as, for example, metal, an alloy, steel, etc. Alternatively, also a stiff synthetic material, wood, etc. provide options. Furthermore, according to a further development, it is provided that the hose carrier unit has also a clearly higher weight than the (empty) flexible hose. Especially according to a further development, the above bending stiffness ratios are advantageous.

In a further development, in the region of the hose entrance and the hose exit outside of the hose carrier unit, a clamping unit is provided, by which a flexible hose led in use around the loop-shaped outer contour is tightenable against the loop-shaped outer contour. In a further development, the clamping unit includes in the region of the hose entrance and the hose exit, on both sides of the symmetry plane, movable clamping elements, wherein, by reducing the distance between the respective clamping element and the symmetry plane, a flexible hose led in use around the loop-shaped outer contour is tightenable against the loop-shaped outer contour and wherein the clamping elements are securable in at least one position with reduced distance to the symmetry plane. With such a clamping unit, a flexible hose can be clamped rapidly and simply into the measuring transducer. According to a further development, in such case, a number of different, securable positions of the clamping elements are provided, so that hoses with different hose diameters are mountable in the measuring transducer. Furthermore, according to a further development, it is provided that the clamping unit has at least one counterpart affixed relative to a housing or a carrier component, so that the flexible hose is clampable tightly between respective clamping elements and counterparts. Both the clamping elements as well as also the at least one counterpart can be formed, for example, by cylinders or rollers.

The present invention relates, furthermore, to a Coriolis, flow measuring device for a fluid flowing in a flexible hose, wherein the measuring device includes a measuring transducer of the invention, which, in given cases, is supplementally embodied according to one of the above explained variants, as well as an electronics, by which measuring signals of the at least one oscillation sensor can be evaluated for determining at least one physical measured variable of the flowing fluid. A manner of functioning of such a Coriolis, flow measuring device has already been explained above. The physical measured variable of the fluid flowing can be especially a mass flow, a density or the like of the flowing fluid.

In a further development, the electronics is embodied in such a manner that, after insertion of an empty, flexible hose into the measuring transducer, a zero point calibration is performable for the specific hose and the parameters determined in such case are applicable for following flow measurements of fluid flowing through this hose. In this way, depending on application, different, flexible hoses can be applied in combination with the Coriolis, flow measuring device. The terminology "following flow measurements" refers especially to mass flow measurement, density measurement and/or a detection of localized impurities (for example, bubbles in a liquid).

In a further development, the electronics is embodied in such a manner that, in use of the Coriolis, flow measuring device with flexible hose installed in the measuring transducer and flowed through by fluid, it can monitor at least one measurement signal registered in a first oscillatory system for the occurrence of an anomaly for detection of a localized contamination entrained in the flowing fluid. In case such an anomaly is detected in the first oscillatory system, the electronics can further monitor whether, after an expected time interval, a corresponding anomaly occurs in the second oscillatory system in at least one measurement signal registered in the second oscillatory system. In case such an anomaly is detected in the second oscillatory system after the expected time interval, the electronics can signal the passing of a localized contamination. Such a detection mechanism is advantageous in many applications, for example, in order in the case of passing of a localized contamination to correct a measured value and/or to issue an alarm or an error report. If the electronics signals the passing of a contamination, this can be used not only internally in the Coriolis, flow measuring device. For example, it can be provided that this is signaled alternatively or supplementally to a user and/or to a communication connected, superordinated control unit. A localized contamination is formed, for example, by a gas bubble entrained in liquid and/or by a solid particle entrained in liquid or gas.

Especially, the electronics is embodied in such a manner that it (at least after activation of the detection function) performs such a detection function regularly during operation of the Coriolis, flow measuring device. The monitored measurement signal is formed, for example, by a phase difference signal, a mass flow, an integrated mass, a resonant frequency of the oscillation, and/or an attenuation of the oscillation, wherein this measurement signal is registered, determined and/or processed in the Coriolis, flow measuring device, in each case, with reference to the oscillatory system in question. An "anomaly" in the measurement signal is, in such case, a typical, temporary disturbance or deviation of the measurement signal caused by a contamination as it passes through the oscillatory system. The "expected time interval" can be a fixed, constant value. It can, however, also be determined as a function of the actual flow velocity of the fluid, as obtainable, for example, from the measured mass flow rate. In a further development, first of all, only the upstream oscillatory system monitors for the occurrence of an anomaly of the measurement signal (the flow direction is, as a rule, known to the electronics) and, in given cases, the additional, above described steps are performed, in case such an anomaly is registered in the first oscillatory system.

BRIEF DESCRIPTION OF THE DRAWINGS

Other advantages and utilities of the invention will become evident based on the following description of an example of an embodiment with reference to the appended drawing, the figures of which show as follows.

DETAILED DISCUSSION IN CONJUNCTION WITH THE DRAWINGS

Figure 1:
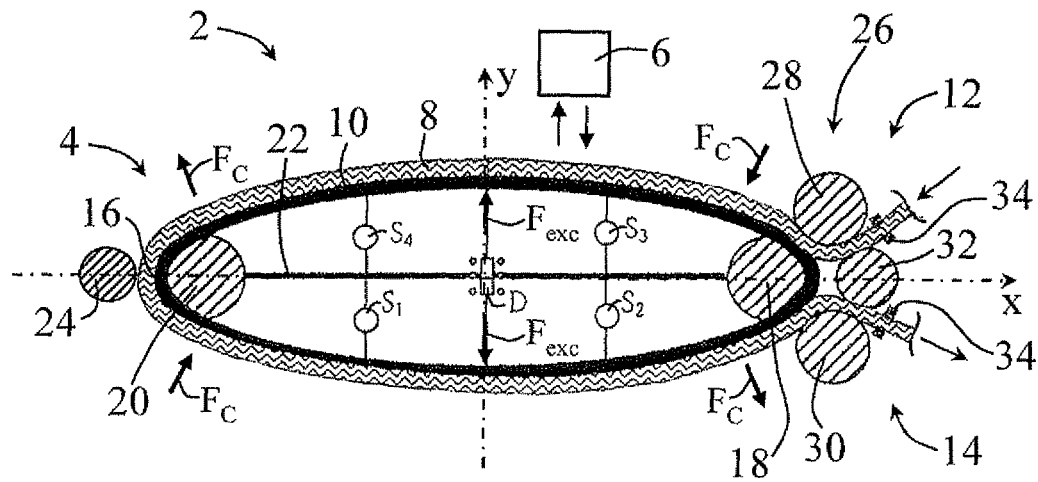
FIG. 1 is a schematic representation of a Coriolis, flow measuring device according to a form of embodiment of the present invention in cross sectional view, wherein a first excited state is presented.
Figure 2:
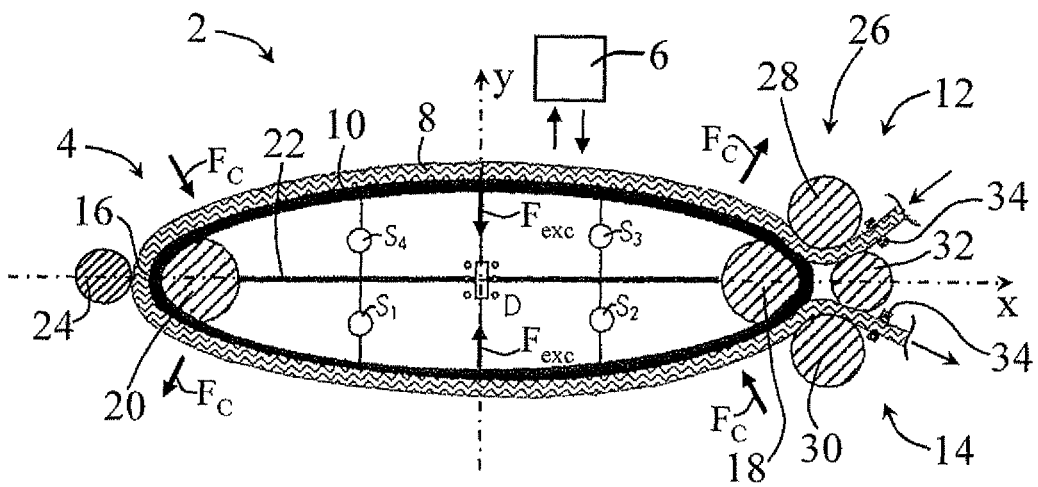
FIG. 2 is a schematic representation of the Coriolis, flow measuring device illustrated in FIG. 1, wherein a second excited state is presented.

The Coriolis, flow measuring device 2 shown in FIGS. 1 and 2 includes a measuring transducer 4 and an electronics 6. Measuring transducer 4 is, in such case, in FIGS. 1 and 2 presented in use with a flexible hose 8 mounted in the measuring transducer 4. Measuring transducer 4 includes a hose carrier unit 10, which has in the region, in which the hose carrier unit 10 is in use in contact with the flexible hose 8, a loop-shaped outer contour. The flexible hose 8 is led around this loop-shaped outer contour. The flexible hose 8 forms in the region along the loop-shaped outer contour a loop shape, by which a loop plane is defined. The loop plane corresponds in the representations of FIGS. 1 and 2 to the xy-plane, which is spanned by the shown x-axis and y-axis. The illustrations of FIGS. 1 and 2 show, in each case, a cross sectional view of the Coriolis, flow measuring device 2 along this loop plane (respectively, the xy-plane).

In the loop plane (respectively, xy-plane), the hose carrier unit 10 (respectively, its cross section in the loop plane) has, in the case of the present form of embodiment, a closed, oval shape. Here, the oval shape is in the form of an ellipse. The longer half axis of this ellipse extends along the x-axis, while the shorter half axis of the ellipse extends along the y-axis. Perpendicularly to the x- and the y-axis, there extends the z-axis (not shown), which is referred to in part for explanation of the figures.

As evident based on FIGS. 1 and 2, the hose carrier unit 10 is arranged mirror symmetrically to the xz-plane, which is referred to as the symmetry plane. The symmetry plane (xz-plane) extends, in such case, between a hose entrance 12 (of the flexible hose 8) to the hose carrier unit 10 and a hose exit 14 (of the flexible hose 8) from the hose carrier unit 10. The loop-shaped outer contour has on the side lying opposite the hose entrance 12 and hose exit 14 a reversal point 16 (respectively, maximum of the loop-shaped arc), through which the symmetry plane (xz-plane) likewise extends. Furthermore, the symmetry plane (xz-plane) is perpendicular to the loop plane (xy-plane).

Also, the hose course of the flexible hose 8 installed in the measuring transducer 4 is, at least in the region, in which the hose 8 lies on the loop-shaped outer contour of the hose carrier unit 10, mirror symmetric to the symmetry plane (xz-plane). Furthermore, the hose course of the flexible hose 8 is in the case of the illustrated form of embodiment also mirror symmetric to the symmetry plane (xz-plane) in the region of the hose entrance 12 and the hose exit 14.

Provided inside the hose carrier unit 10 are, respectively, a first securement 18 and a second securement 20. Securements 18, 20 are arranged on the symmetry plane. The first securement 18 is, in such case, arranged in the region of the hose entrance 12 and the hose exit 14, while the second securement 20 is arranged in the region of the reversal point 16 of the loop-shaped outer contour. In the illustrated form of embodiment, the securements 18, 20 are formed by dowels, whose outer diameters are matched to the inner diameters of the hose carrier unit 10 in the relevant regions. Securements 18 and 20 are, in such case, in such close contact with the hose carrier unit 10 that oscillation of the hose carrier unit 10 in the region of the symmetry plane (xz-plane) is completely or at least largely suppressed. Accordingly, the hose carrier unit 10 is divided by the securements 18, 20 into two oscillation systems arranged mirror symmetrically to one another relative to the symmetry plane (xz-plane).

Securements 18 and 20 are, in such case, preferably arranged fixed relative to one another. This can occur, for example, via a corresponding cross brace 22, which extends between the two securements 18, 20. Furthermore, it is preferably provided that the securements 18, 20 are also arranged locationally fixed relative to the external environment of the Coriolis, flow measuring device 2, in order to prevent an oscillation of the total Coriolis, flow measuring device 2 relative to the external environment. For this, for example, a securement section can be provided, via which the securements 18, 20, or a component fixedly connected with the securements 18, 20 (such as, for example, the cross brace 22) are securable to a securement point provided in the external environment. A component fixedly connected with the securements 18, 20 can be formed especially by a housing- or carrier component (not shown) of the Coriolis flow measuring device 2 or by the cross brace 22.

In the region of the reversal point 16 of the loop-shaped outer contour, a hose securement 24 is supplementally provided outside of the hose carrier unit 10 on the symmetry plane (xz-plane). In the case of the present form of embodiment, hose securement 24 is formed by a component movable in the loop plane (xy-plane), such as, for example, a swingable dowel. Hose securement 24 is, in such case, securable at different distances from the reversal point 16, so that different hose sizes can be clamped between the hose securement 24 and the hose carrier unit 10 in the region of the reversal point 16.

On the side lying opposite the reversal point 16 (and therewith in the region of the hose entrance 12 and the hose exit 14), outside of the hose carrier unit 10, a clamping unit 26 is provided, by which in use a flexible hose 8 led around the loop-shaped outer contour is tightenable against the loop-shaped outer contour. Clamping unit 26 includes two clamping elements 28, 30, which are movable at least in the xy-plane. In the case of the present form of embodiment, the clamping elements 28, 30 are formed by dowels or rollers. In such case, the clamping element 28 is arranged in the region of the hose entrance 12 (shown above in FIGS. 1 and 2), while the other clamping element 30 is arranged in the region of the hose exit 14 (shown below in FIGS. 1 and 2). On the symmetry plane (xz-plane) and outside of the hose carrier unit 10, there is provided, furthermore, a fixedly arranged clamp-counterpart 32. The clamping elements 28, 30 are in the case of the present form of embodiment arranged mirror symmetrically to one another relative to the symmetry plane (xz-plane).

The clamping elements 28, 30 are embodied in such a manner that their distance from the symmetry plane (xz-plane), especially from the clamp-counterpart 32 and from the hose carrier unit 10, can be increased and decreased according to need. Especially, the clamping elements 28, 30 can be swingably embodied in the xy-plane. The clamping elements 28, 30 are, in such case, securable (respectively, engageable) at different distances from the clamp-counterpart 32 and the hose carrier unit 10, so that different hose sizes can be clamped between the respective clamping elements 28, 30 and the clamp-counterpart 32 as well as the hose carrier unit 10. The clamping elements 28, 30 are preferably arranged in a position, in which a flexible hose 8 is clamped between them and the clamp-counterpart 32 as well as the hose carrier unit 10, in the region of the hose carrier unit 10, in which oscillation of the hose carrier unit 10 completely or at least largely is suppressed by the first securement 18 (e.g. lying directly opposite the first securement 18). In this way, it is prevented that the clamping elements 28, 30 are caused to oscillate and/or the flexible hose is squeezed periodically.

The explained construction of the measuring transducer 4 enables, in such case, that a flexible hose 8 can be mounted easily in the measuring transducer 4. Before insertion of a flexible hose 8, the hose securement 24 and the clamping elements 28, 30 are opened, which means that their separation, in each case, from the hose carrier unit 10 (and in the case of the clamping elements 28, 30 supplementally from the clamp-counterpart 32) is increased. In this state, a flexible hose 8 can be easily led around the loop-shaped outer contour of the hose carrier unit 10. Then, the clamping elements 28, 30 are moved toward the clamp-counterpart 32 and the hose carrier unit 10, so that the flexible hose is clamped between the clamping elements 28, 30 and the clamp-counterpart 32 as well as the hose carrier unit 10 and simultaneously tightened around the loop-shaped outer contour of the hose carrier unit 10. The clamping elements 28, 30 are secured in a suitable position. At the same time, or, in time, offset from the clamping by the clamping element 28, 30, also the hose securement 24 is moved toward the hose carrier unit 10 (respectively, toward the reversal point 16), so that the flexible hose 8 is clamped between the hose securement 24 and the hose carrier unit 10. The hose securement 24 is affixed in a suitable position.

Because the clamping unit 26 is arranged in the region of the hose entrance 12 and the hose exit 14 and the separation between the two arc sections of the hose carrier unit 10 arranged above and below the symmetry plane (xz-plane) is reduced in this region (due to the oval shape of the hose carrier unit 10) compared with the central region (region of the yz-plane) of the hose carrier unit 10 (i.e. the U-shape is narrowed in the region of the upper ends of the "U"), during the clamping of the flexible hose 8 by the clamping unit 26, a tensile force is exerted on the flexible hose 8. As a result, the flexible hose 8 is tensioned by the clamping unit 26, due to the loop shape narrowing in the region of the clamping unit 26, against and around the loop-shaped outer contour of the hose carrier unit 10.

In given cases, the flexible hose 8 can be elastically extensible in its length, so that it is clamped in the clamping procedure by the clamping unit 26 with a corresponding tension around the hose carrier unit 10. Furthermore, it can be provided that on the flexible hose 8 at defined intervals (along the hose 8) corresponding detent elements (e.g. protrusions) are provided, which during the clamping by the clamping unit 26 (especially through the clamping elements 28, 30) securely engage, respectively become clamped, and therewith prevent a slipping through of the flexible hose. In this way, a desired and predefined tension can be achieved in the flexible hose 8. In FIGS. 1 and 2, such detent elements are shown, by way of example, by protrusions 34, which, in each case, engage between the clamping elements 28, 30 and the clamp-counterpart 32 and prevent slip through of the flexible hose 8.

The clamping force between the hose securement 24 and the hose carrier unit 10 as well as the clamping force between the respective clamping elements 28, 30 and the clamp-counterpart 32 as well as the hose carrier unit 10 are preferably determined as a function of the respective inherent stiffness of the flexible hose 8 installed in the measuring transducer 4 and/or as a function of the pressure of the fluid flowing within the hose 8. Preferably, the clamping force is selected sufficiently high that in the region of the hose securement 24 and in the region of the clamping unit 26 an oscillation of the relevant, flexible hose 8 is at least largely suppressed. Preferably, the hose 8 is only pressed together, or squeezed, to an extent that does not disadvantageously increase the flow resistance.

The applied, flexible hose 8 can be formed, in such case, by a continuous hose, which is not pieced together for the performing of a measurement by the Coriolis, flow measuring device 2. Alternatively, the installed flexible hose 8 can also be a hose section, which is connected via corresponding connecting pieces (not shown) into a pipeline, etc. Especially, the installed flexible hose 8 can be a cost effective, consumed part, or wear part (respectively, disposable article), which, after the use, is discarded and replaced by a new one. Especially, in latter case, the flexible hose 8 can be provided as a mass produced article especially for use in the Coriolis, flow measuring device. The flexibility of the hose 8 is, in such case, preferably selected in such a manner that the hose contributes not at all or not noticeably to the stiffness of the oscillatory system (composed of hose carrier unit 10 and hose 8). This increases the accuracy of measurement of the Coriolis, flow measuring device 2. For example, the flexible hose 8 can be formed by a flexible, synthetic material. The hose can, in such case, be reinforced by a stable material (in the form of a net, helix, etc.) incorporated in the hose wall, so that the hose 8 has even in bent and/or clamped regions a largely constant inner diameter. The hose carrier unit can be formed, for example, of a metal or an alloy.

The hose carrier unit 10 is embodied here also mirror symmetrically relative to a plane (hereinafter, the yz-plane)

extending perpendicularly to the symmetry plane (xz-plane) and perpendicularly to the loop plane (xy-plane). As evident based on FIGS. 1 and 2, also the hose course of a flexible hose 8 installed in the measuring transducer 4 is embodied essentially mirror symmetric relative to this yz-plane. Solely in the region of the hose entrance 12 and the hose exit 14 does the hose course deviate from the hose course in the region of the reversal point 16. By a corresponding securement of the hose carrier unit 10 by the two securements 18, 20 as well as, in given cases, of the flexible hose 8 by the hose securement 24 and the clamping unit 26, the two oscillatory systems (formed above and below the symmetry plane, or xz-plane) can, with reference to oscillatory characteristics, nevertheless be formed, in each case, largely symmetrically relative to the yz-plane.

Arranged inside the hose carrier unit 10 are an exciter D (actually formed of two sub-exciters) and four oscillation sensors $S_1$, $S_2$, $S_3$ and $S_4$. In the present form of embodiment, exciter D is an electromechanical exciter. Exciter D is centrally affixed on the cross brace 22 and coupled with its two distal ends mechanically to corresponding arc sections of the hose carrier unit 10. Upon excitation to oscillate, the exciter D (respectively, its two sub-exciters extending, respectively, between the cross brace 22 and the associated arc section) alternatingly enlarge and reduce the separation of the arc sections of the hose carrier unit 10 extending between the securements 18, 20 relative to the cross brace 22. The two oscillatory systems execute accordingly oscillations, which are mirror symmetric to one another (relative to the symmetry plane, i.e. the xz-plane). The oscillations are accompanied, in each case, by alternating elastic deformations of the hose carrier unit 10, especially of the two arc sections of the hose carrier unit 10 extending between the securements 18, 20. This is shown in FIGS. 1 and 2 schematically by the representation of two excitement states. In such case, in FIG. 1, the excitation force $F_{exc}$ exerted by the exciter D on the two arc sections is, in each case, directed outwardly (i.e. away from the symmetry plane), so that the separation between the two arc sections is enlarged. FIG. 2 shows the excitation force $F_{exc}$ exerted by the exciter D on the two arc sections, in each case, directed inwardly, (i.e. toward the symmetry plane), so that the separation between the two arc sections is reduced.

As known from the technical field, due to the oscillation of the hose 8, a Coriolis force acts, in each case, on the moved mass, when fluid is flowing through the flexible hose 8. If a flow direction is assumed, as shown by the arrows in FIGS. 1 and 2, then there acts in the case of the excited state illustrated in FIG. 1 (increasing separation between the two arc sections) in the case of the oscillatory system located upstream (shown above in FIGS. 1 and 2) in the region of the first securement 18 (and somewhat downstream of such) the inwardly directed Coriolis force Fc (i.e. directed toward the hose carrier unit 10). Furthermore, there acts in the case of the oscillatory system located upstream in the region of the second securement 20 (and somewhat upstream of such) the outwardly directed Coriolis force Fc. In the case of the downstream located oscillatory system (shown below in FIGS. 1 and 2), there acts in the region of the second securement 20 (and somewhat downstream of such) the inwardly directed Coriolis force Fc, while, in the region of the first securement 18 (and somewhat upstream of such) such acts outwardly. In the case of the excited state illustrated in FIG. 2 (reduction of the distance between the two arc sections), the Coriolis force Fc acts, in each case, oppositely to the direction explained with reference to the excited state of FIG. 1. The direction of the Coriolis forces Fc in FIG. 2 is shown in the corresponding regions.

Each oscillatory system also has two oscillation sensors. These are arranged, in each case, spaced from one another along the associated arc section of the hose carrier unit 10. Especially, the upstream oscillatory system (shown above in FIGS. 1 and 2) has the oscillation sensors $S_3$ and $S_4$, while the downstream oscillatory system (shown below in FIGS. 1 and 2) has the oscillation sensors $S_1$ and $S_2$. The oscillation sensors of each oscillatory system ($S_3$ and $S_4$ of the upstream oscillatory system; $S_1$ and $S_2$ of the downstream oscillatory system) are arranged mirror symmetrically to one another with reference to the yz-plane. Each oscillation sensor $S_1$, $S_2$, $S_3$ and $S_4$ registers oscillations of the respective arc section of the hose carrier unit 10 relative to the cross brace 22. Furthermore, the oscillation sensors of the one oscillatory system (e.g. the oscillation sensors $S_3$ and $S_4$ of the upstream oscillatory system) are arranged mirror symmetrically relative to the symmetry plane (xz-plane) relative to the corresponding oscillation sensors of the other oscillatory system (e.g. the oscillation sensors $S_2$ and $S_1$ of the downstream oscillatory system). The oscillation sensors $S_1$, $S_2$, $S_3$ and $S_4$ in the case of the present form of embodiment are formed, in each case, by electromechanical oscillation sensors, which are coupled, in each case, mechanically to the hose carrier unit 10.

As is clear based on the preceding description, the measuring transducer 4 has two oscillatory systems essentially identical with reference to their oscillatory behavior (both with applied flexible hose 8 as well as also without applied hose). Also, relative to the exciting and registering of the oscillations of the two oscillatory systems, these are, due to the above described symmetries, identical. If a homogeneous fluid flows through the flexible hose, then the oscillation phase difference registered between the sensors $S_3$ and $S_4$ corresponds to the oscillation phase difference registered between the sensors $S_1$ and $S_2$. These two identical oscillatory systems can be applied, in order to obtain additional information with reference to the fluid led in the respectively installed hose. For example, the measuring transducer can, as explained below based on a form of embodiment, register localized contaminations entrained in the fluid, such as, for example, gas bubbles, solid particles, etc., entrained in a liquid. Especially, due to such localized impurities, there can occur, first of all, in the upstream oscillatory system, a shifting of the registered phase difference, and time delayed relative to this, a shifting of the registered phase difference in the downstream oscillatory system.

As is generally known in the technical field, control of the excitation by the exciter D as well as evaluation of the sensor signals provided by the oscillation sensors S1, S2, S3 and S4 is accomplished by a correspondingly embodied electronics 6. This is shown schematically in FIGS. 1 and 2 only by a box. In the case of the present form of embodiment, electronics 6 is embodied for determining mass flow as well as density of the flowing fluid.

In the measuring transducer 4, flexible hoses of different hose size, different flexibility as well as different hose diameter can be applied. The electronics 6 is, in such case, preferably embodied in such a manner that, after insertion of a flexible hose into the measuring transducer 4, first of all, a calibration is performable. The calibration can, in such case, depending on the calibration method, be performed in the case of a known mass flow, in the case of hose filled with fluid without flow or preferably with empty hose. The parameters determined in the calibration are then applied for flow measurement with the particular flexible hose.

Furthermore, the electronics is 6 embodied in such a manner that in use of the Coriolis, flow measuring device 2 a localized contamination entrained in the flowing fluid is detectable. Such a contamination can be, for example, a gas bubble entrained in liquid or a solid particle entrained in liquid or gas. If this detection mechanism is activated, then the electronics 6 monitors whether at one of the two oscillatory systems an anomaly occurs in the case of at least one measurement signal registered for this oscillatory system, such as, for example, the registered mass flow or the registered resonant frequency. An anomaly is, in such case, a typical disturbance or deviation of the measurement signal triggered by a contamination as it passes through the oscillatory system. Preferably, in such case, only the upstream oscillatory system monitors for the occurrence of such an anomaly (the flow direction is, as a rule, known to the electronics 6). In case such an anomaly is detected in the first oscillatory system, then the electronics 6 monitors whether, after an expected time interval, there occurs in the second (downstream) oscillatory system a corresponding anomaly in at least one measurement signal registered in the second oscillatory system. The expected time interval is determined in the case of the present form of embodiment as a function of the mass flow registered by the Coriolis, flow measuring device 2. In case the second oscillatory system, after expiration of the expected time interval, signals that such an anomaly has been detected, then a localized contamination has passed through the Coriolis, flow measuring device. This information can be utilized in the Coriolis, flow measuring device 2 or by a superordinated control unit for correction of the registered mass flow, the registered density and/or for triggering an alarm.

Figure 3:
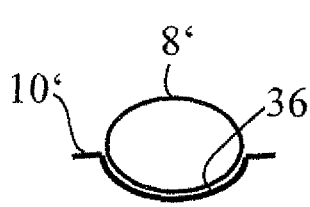
FIG. 3 is a schematic representation of a cross sectional view through an arm of the hose carrier unit and through a flexible hose led around the hose carrier unit according to a form of embodiment of the present invention.
Figure 4:
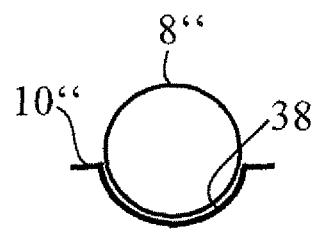
FIG. 4 is a schematic representation of a cross sectional view through an arm of the hose carrier unit and through a flexible hose led around the hose carrier unit according to an additional form of embodiment of the present invention.

FIGS. 3 and 4 show, in each case, schematic cross sectional views of an arm of a hose carrier unit 10', 10" and a flexible hose 8', 8" led around the hose carrier unit 10', 10" according to two different forms of embodiment. The plane of the cross section extends, in each case, perpendicular to the direction of elongation of the respective hose 8', 8", or the direction of elongation of the respective arm of the hose carrier unit 10', 10". The hose carrier unit 10, 10" is in the case of these forms of embodiment, in each case, formed by a rail-like carrier. This carrier can be, for example, oval, as presented in FIGS. 1 and 2 of the hose carrier unit 10. In the case of both forms of embodiment illustrated in FIGS. 3 and 4, the hose carrier unit 10', or 10", comprises a gutter 36, or 38, extending along the loop-shaped outer contour for receiving a flexible hose 8', or 8".

In the case of both forms of embodiment of FIGS. 3 and 4, the rounding of the gutter 36, respectively 38, corresponds essentially to the rounding of the part of the hose 8', or 8", which lies on the gutter 36, or 38, as the case may be. In the case of the form of embodiment illustrated in FIG. 3, the hose 8' has an oval cross section, wherein the hose part with the greater radius of curvature lies on the gutter 36. Such an arrangement can also be used in the case of a flexible hose, which has a circularly shaped cross section, which, however, due to the bearing on the relevant hose carrier unit, is reduced to an oval cross section. In the case of the form of embodiment illustrated in FIG. 4, the hose 8" has a circularly shaped cross section.

The invention claimed is:

1. A measuring transducer of the vibration-type for a fluid flowing in a flexible hose, comprising:
 a hose carrier unit, having a hose course, forming at least sectionally a loop-shaped outer contour with arc sections, around which the flexible hose can be led;
 a clamping unit having the flexible hose led around said loop-shaped outer contour and tightenable against said loop-shaped outer contour;
 at least one exciter coupled to said hose carrier unit and exciting said hose carrier unit to execute mechanical oscillations; and
 at least one oscillation sensor registering mechanical oscillations of said hose carrier unit and/or the flexible hose installed in the measuring transducer.

2. The measuring transducer as claimed in claim 1, wherein:
 said hose carrier unit and the hose course of the flexible hose installed in the measuring transducer extend mirror symmetrically with reference to a symmetry plane (xz-plane); and
 the symmetry plane extends between a hose entrance of said hose carrier unit and a hose exit of said hose carrier unit, extends from a reversal point of said loop-shaped outer contour located lying opposite said hose entrance and said hose exit and is, furthermore, perpendicular to a loop plane, which is defined by the loop shape of the flexible hose installed in the measuring transducer.

3. The measuring transducer as claimed in claim 2, wherein:
 said hose carrier unit is divided by a securement arranged on the symmetry plane in the region of said hose entrance and said hose exit as well as by a securement arranged on the symmetry plane in the region of said reversal point into two oscillatory systems arranged mirror symmetrically to one another relative to the symmetry plane.

4. The measuring transducer as claimed in claim 3, wherein: said two oscillatory systems are excitable to mutually symmetric oscillations by said at least one exciter by alternating enlarging and reducing of the separation of the arc sections of said hose carrier unit extending between said securements.

5. The measuring transducer as claimed in claim 3, wherein: there are associated with each oscillatory system, two oscillation sensors, which, are arranged spaced from one another along an associated arc section of said hose carrier unit extending between said securements.

6. The measuring transducer as claimed in claim 3, wherein:
 said two oscillatory systems, with reference to an arrangement of the oscillation measurement points of said at least one oscillation sensor and with reference to excitation points of said at least one exciter, are embodied mirror symmetrically to one another relative to the symmetry plane.

7. The measuring transducer as claimed in claim 3, wherein: said hose carrier unit, a predetermined course of a flexible hose installed in the measuring transducer, apart from the region of said hose entrance and said hose exit and the region of the reversal point, an arrangement of the oscillation measurement points of said at least one oscillation sensor, and/or an arrangement of the excitation points of said hose carrier unit by said at least one exciter are mirror symmetric relative to a plane extending perpendicular to the symmetry plane and perpendicular to a loop plane.

8. The measuring transducer as claimed in claim 1, wherein:
 said hose carrier unit has, in a loop plane defined by the loop shape of the flexible hose installed in use in the measuring transducer, a closed shape.

9. The measuring transducer as claimed in claim 8, wherein:
 said closed shape comprises an oval shape.

10. The measuring transducer as claimed in claim 1, wherein:

said at least one exciter and/or said at least one oscillation sensor is/are arranged inwardly of said hose carrier unit.

11. The measuring transducer as claimed in claim 1, wherein: said hose carrier unit includes a gutter extending along the loop-shaped outer contour for accommodating the flexible hose installed in the measuring transducer.

12. The measuring transducer as claimed in claim 1, wherein:
the flexible hose is formed at least partially of a flexible synthetic material and/or a flexible weave.

13. The measuring transducer as claimed in claim 1, wherein:
said hose carrier unit has a clearly higher bending stiffness than the flexible hose, that a ratio of the bending stiffness of said hose carrier unit along the loop-shaped outer contour to the bending stiffness of the hose along its direction of elongation is at least 10.

14. The measuring transducer as claimed in claim 1, wherein: said clamping unit has movable clamping elements in the region of a hose entrance and a hose exit on both sides of a symmetry plane the flexible hose led around the loop-shaped outer contour by reducing the distance between the respective clamping elements and the symmetry plane, and said clamping elements are securable in at least one position with reduced distance to the symmetry plane.

15. A Coriolis, flow measuring device for a fluid flowing in a flexible hose, comprising: a measuring transducer including: a hose carrier unit having at least sectionally a loop-shaped outer contour; around which the flexible hose can be led; a clamping unit, the flexible hose is led around said loop-shaped outer contour and tightenable against said loop-shaped outer contour; at least one exciter coupled to said hose carrier unit for exciting said hose carrier unit to execute mechanical oscillations, and at least one oscillation sensor, for registering mechanical oscillations of said hose carrier unit and/or the flexible hose installed in the measuring transducer electronics for evaluating measuring signals of said at least one oscillation sensor for determining at least one physical measured variable of the flowing fluid.

16. The Coriolis, flow measuring device as claimed in claim 15, wherein:
said electronics is embodied in such a manner that, after insertion of an empty, flexible hose into the measuring transducer, a zero point calibration is performable for the specific hose and the parameters determined in such case are applicable for following flow measurements of fluid flowing through this hose.

17. The Coriolis, flow measuring device as claimed in claim 15, wherein:
said electronics is embodied in such a manner that it can, in use of the Coriolis, flow measuring device with flexible hose, which is installed in the measuring transducer for providing a first oscillatory system and a second oscillatory system downstream said first oscillatory system, and which is flowed-through by fluid, for detection of a localized contamination entrained in the fluid flowing, monitor at least one measurement signal registered in the first oscillatory system for the occurrence of an anomaly, in case such an anomaly is detected in the first oscillatory system, monitor whether, after an expected time interval, in the second oscillatory system, a corresponding anomaly occurs in at least one measurement signal registered in the second oscillatory system, and, in case such an anomaly is detected in the second oscillatory system after the expected time interval, the passing of a localized contamination can be signaled.

* * * * *